(12) United States Patent
Osoegawa et al.

(10) Patent No.: US 11,752,278 B2
(45) Date of Patent: Sep. 12, 2023

(54) MESH NEBULIZER (71) Applicant: OMRON HEALTHCARE CO., LTD., Muko (JP)

(72) Inventors: Nobuhiko Osoegawa, Kyoto (JP); Hiroyuki Shino, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 1227 days.

(21) Appl. No.: 16/291,005

(22) Filed: Mar. 4, 2019

(65) Prior Publication Data
US 2019/0192791 A1    Jun. 27, 2019

Related U.S. Application Data (63) Continuation of application No. PCT/JP2017/027291, filed on Jul. 27, 2017.

(30) Foreign Application Priority Data

Sep. 8, 2016    (JP) .................................. 2016-175729

(51) Int. Cl.
*A61M 11/00*    (2006.01)
*A61M 15/00*    (2006.01)
*B05B 17/00*    (2006.01)

(52) U.S. Cl.
CPC ........... *A61M 11/005* (2013.01); *A61M 11/00* (2013.01); *A61M 15/0085* (2013.01);
(Continued)

(58) Field of Classification Search
CPC ............... A61M 11/005; A61M 15/001; B05B 17/0638
See application file for complete search history.

(56) References Cited

U.S. PATENT DOCUMENTS

| | | | |
|---|---|---|---|
| 2004/0050953 A1* | 3/2004 | Terada | B05B 17/0623 239/102.2 |
| 2010/0219263 A1 | 9/2010 | Feriani et al. | |

(Continued)

FOREIGN PATENT DOCUMENTS

| | | |
|---|---|---|
| CN | 109152888 A | 1/2019 |
| JP | 58-216066 A | 12/1983 |

(Continued)

OTHER PUBLICATIONS

Official Communication issued in International Patent Application No. PCT/JP2017/027291, dated Oct. 31, 2017.
(Continued)

*Primary Examiner* — Samchuan C Yao
*Assistant Examiner* — Tina Zhang
(74) *Attorney, Agent, or Firm* — KEATING AND BENNETT, LLP (57) ABSTRACT

A mesh nebulizer that atomizes and ejects liquid through a mesh portion includes a vibration portion including a vibration surface facing upward, a liquid supply portion that supplies liquid toward the vibration surface of the vibration portion, a sheet including the mesh portion, and a support frame that supports a peripheral edge of the sheet. The support frame includes a bottom plate that supports a lower surface of the peripheral edge of the sheet, the bottom plate having a flat annular shape, and a larger inner diameter than a diameter of the vibration surface, and a protrusion radially protruding inward from the bottom plate. The sheet including the mesh portion faces the vibration surface at an inclination angle and is in contact with a first portion of a peripheral edge of the vibration surface.

5 Claims, 10 Drawing Sheets (52) U.S. Cl.
CPC ........ *B05B 17/0646* (2013.01); *A61M 11/001* (2014.02); *A61M 2202/04* (2013.01)

(56) References Cited

U.S. PATENT DOCUMENTS

| | | | |
|---|---|---|---|
| 2012/0266870 A1* | 10/2012 | Denyer | A61M 15/0085 128/200.14 |
| 2012/0279533 A1* | 11/2012 | Kato | B08B 3/102 134/184 |
| 2019/0054258 A1 | 2/2019 | Koike et al. | |
| 2019/0209790 A1* | 7/2019 | Maeda | B06B 3/00 |

FOREIGN PATENT DOCUMENTS

| | | | | |
|---|---|---|---|---|
| JP | 2010-119845 A | 6/2010 | | |
| JP | 2012-213472 A | 11/2012 | | |
| JP | 2013-221633 A | 10/2013 | | |
| JP | 2014-4208 A | 1/2014 | | |
| JP | 2014-4211 A | 1/2014 | | |
| JP | 2014004208 A | * | 1/2014 | .......... A61M 11/005 |

OTHER PUBLICATIONS

Official Communication issued in corresponding Chinese Patent Application No. 201780054847.X, dated Oct. 22, 2020.

\* cited by examiner

MESH NEBULIZER

CROSS REFERENCE TO RELATED APPLICATIONS

This application claims the benefit of priority to Japanese Patent Application No. 2016-175729 filed on Sep. 8, 2016 and is a Continuation Application of PCT Application No. PCT/JP2017/027291 filed on Jul. 27, 2017. The entire contents of each application are hereby incorporated herein by reference.

BACKGROUND OF THE INVENTION

1. Field of the Invention

The present invention relates to a mesh nebulizer, and more particularly to a mesh nebulizer that atomizes and ejects liquid supplied between a vibration surface and a mesh portion, through the mesh portion.

2. Description of the Related Art

Conventionally, this kind of mesh nebulizer as disclosed in Japanese Patent Application Laid-Open No. 2014-4208 including a horn vibrator provided in a main body, and a mesh cap detachably and openably (rotatably) attached to the main body has been known. In the state in which the mesh cap is attached to the main body and the main body is closed, the vibration surface (the surface of a tip) of the horn vibrator faces the thin plate-shaped mesh portion of the mesh cap. In this state, medical liquid is supplied between the vibration surface and the mesh portion, and a drive voltage is applied to the horn vibrator to vibrate the vibration surface. As a result, the medical liquid is atomized and ejected through the mesh portion.

In the mesh nebulizer, by inclining the vibration surface of the horn vibrator with respect to an entrance surface (a surface facing the vibration surface) of the mesh portion, it is configured such that a gap between the entrance surface and the vibration surface is optimized at any location of the mesh portion.

However, in the mesh nebulizer, the mesh portion is supported by a reinforcing part having an outer diameter larger than the diameter of the vibration surface, and is in contact with the vibration surface only at one position of the peripheral edge of the vibration surface. The reinforcing part is separated from the vibration surface. For this reason, if the mesh portion is made of, for example, a sheet made of a synthetic resin, there is a problem that the sheet is deflected and the inclination accuracy between the vibration surface and the mesh portion (entrance surface) becomes insufficient. Further, in order to incline the vibration surface of the horn vibrator with respect to the entrance surface of the mesh portion by a predetermined angle, a plurality of members are required.

SUMMARY OF THE INVENTION

Thus, preferred embodiments of the present invention provide mesh nebulizers that improve accuracy of inclination of a sheet including a mesh portion with respect to a vibration surface of a horn vibrator without increasing a number of elements or members, and stably atomizes liquid.

A mesh nebulizer according to a preferred embodiment of the present invention is a mesh nebulizer that atomizes and ejects liquid through a mesh portion includes a vibration portion having a vibration surface facing upward, a liquid supply portion that supplies liquid toward the vibration surface of the vibration portion; a sheet including the mesh portion; and a support frame that supports a peripheral edge of the sheet, wherein the support frame includes a bottom plate that supports a lower surface of the peripheral edge of the sheet, the bottom plate having a flat annular shape, and a larger inner diameter than a diameter of the vibration surface, and a protrusion radially protruding inward from the bottom plate, the sheet including the mesh portion faces the vibration surface with an inclination angle and is in contact with a first portion of a peripheral edge of the vibration surface, and the protrusion of the support frame is in contact with a second portion of the peripheral edge of the vibration surface, the second portion opposing the first portion, and maintains the sheet with respect to the vibration surface at the inclination angle.

In the present specification, the "mesh portion" means a component that includes a plurality of through-holes penetrating the sheet and allows liquid to pass through the through-holes and atomizes the liquid.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Hereinafter, preferred embodiments of the present invention will be described in detail with reference to drawings.

Figure 1:
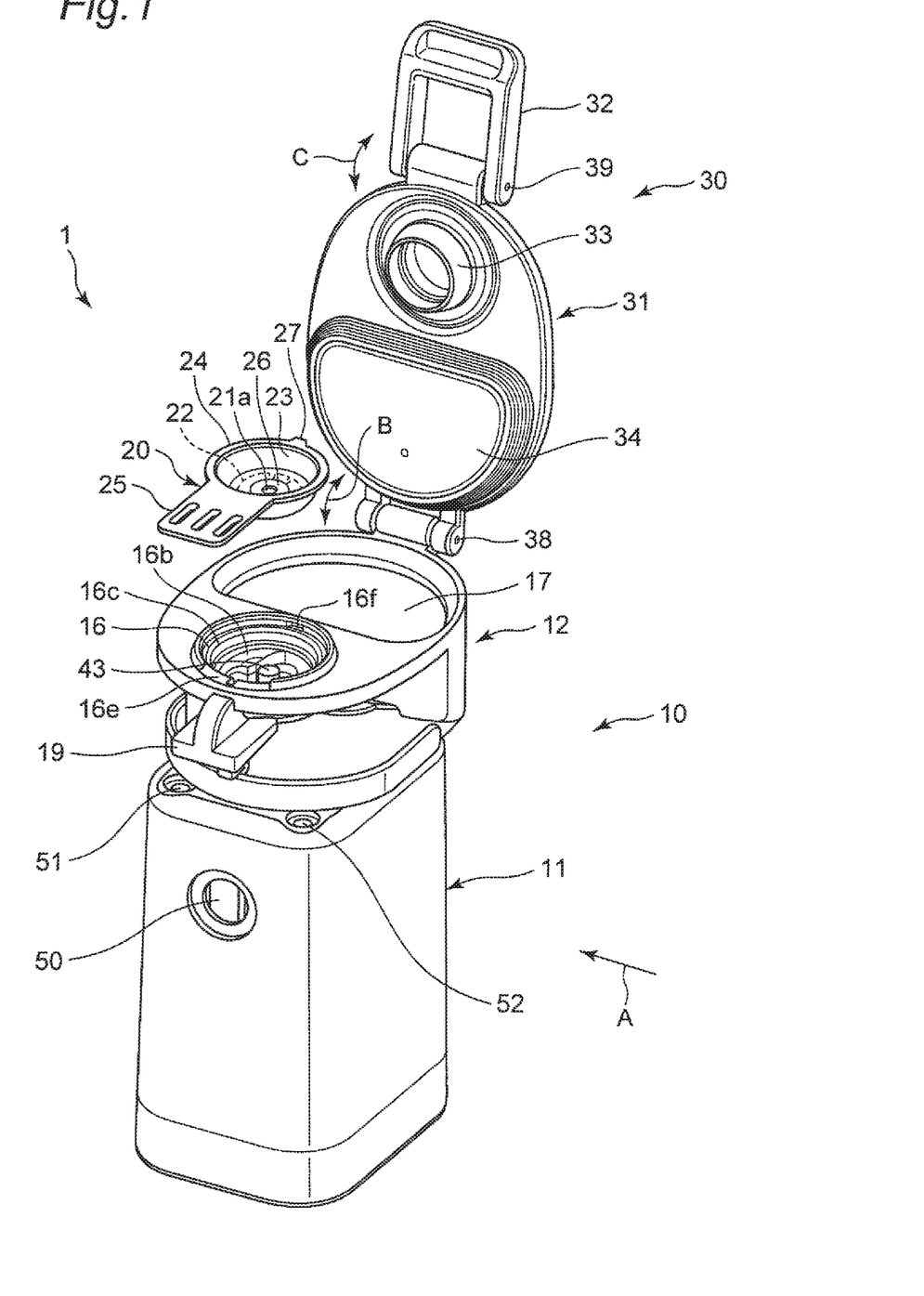
FIG. 1 is a perspective exploded view illustrating a mesh nebulizer in accordance with a preferred embodiment of the present invention.
Figure 2:
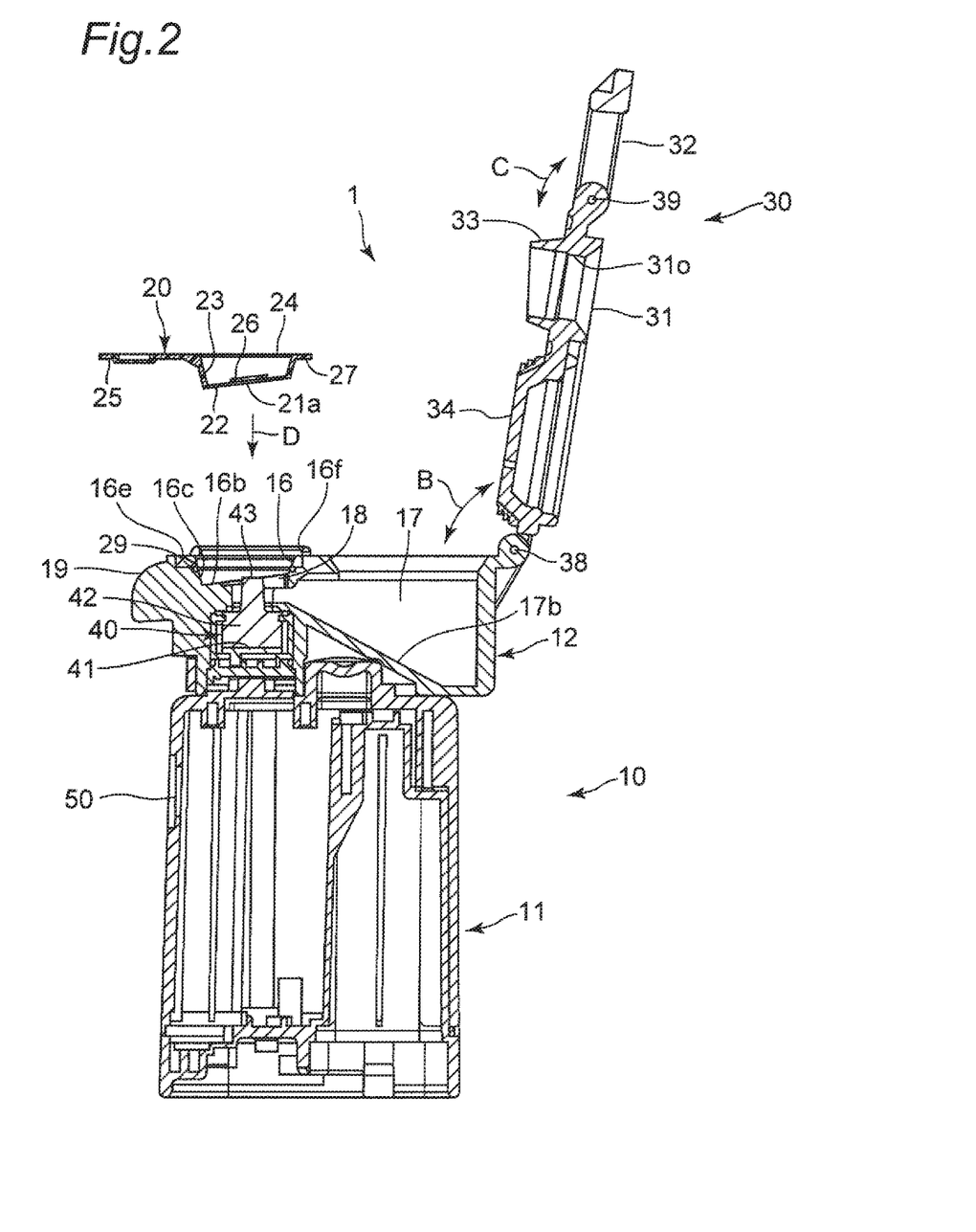
FIG. 2 is a longitudinal sectional view illustrating the mesh nebulizer in the exploded state when viewed from a right side.

FIG. 1 is an exploded view illustrating a mesh nebulizer (indicated by a reference numeral 1) in accordance with a preferred embodiment of the present invention when diagonally viewed. FIG. 2 is a longitudinal sectional view illustrating the mesh nebulizer 1 in the exploded state in FIG. 1 when viewed from right (direction indicated by arrow A in FIG. 1).

As illustrated in FIG. 1 and FIG. 2, the mesh nebulizer 1 includes a main body lower portion 11 having a quadrangular prism or substantially quadrangular prism outer shape, and a main body upper portion 12 having an elliptic columnar outer shape, which is detachably fitted to the main body lower portion 11 from above. The main body lower portion 11 and the main body upper portion 12 define a main body 10.

As illustrated in FIG. 1, a power switch 50 to turn on and off the power of the nebulizer 1 is provided on a front surface of the main body lower portion 11. LED lamps 51 and 52 to notify the operation state of the nebulizer 1 are provided in the upper left corner and the upper right corner on the front side, respectively, on the upper surface of the main body lower portion 11. A control system described later is mainly mounted inside the main body lower portion 11.

A concave portion 16 having a circular or substantially circular planar shape opened upward is provided in a front half region of the upper surface of the main body upper portion 12 so as to receive an exchangeable member 20 described later. As illustrated in FIG. 2, the concave portion 16 includes a bottom surface 16b inclined with respect to the longitudinal axis direction (vertical direction) of the main body 10, and a side surface 16c that is continuous to the bottom surface 16b and gradually becomes larger toward the upper side. As illustrated in FIG. 1, a groove 16e radially extending outward from the concave portion 16 in a particular direction (in this example, toward the front surface) is provided around an upper edge of the concave portion 16 so as to receive a grip portion 25 of the exchangeable member 20 described later. Further, a groove 16f radially extending outward from the concave portion 16 toward the rear surface in this example is provided around the upper edge of the concave portion 16 so as to receive a tip protrusion 27 of the exchangeable member 20 described later. Further, as illustrated in FIG. 2, a packing 29 is provided on the side surface 16c of the concave portion 16 of the main body 10 so as to circumferentially surround and contact a side wall portion 23 of the exchangeable member 20 described later.

In the main body upper portion 12, a vibration portion 40 is provided at a position corresponding to the concave portion 16. The vibration portion 40 includes an ultrasonic vibrator 41 at a position spaced apart downward from the concave portion 16, a vibration surface 43 that is horizontally arranged at a position corresponding to the bottom surface 16b of the concave portion 16 and faces the upper side, and a horn 42 located between the ultrasonic vibrator 41 and the vibration surface 43 to amplify the vibration of the ultrasonic vibrator 41 and transmit the vibration to the vibration surface 43. The drive voltage for the ultrasonic vibrator 41 is supplied from the main body lower portion 11 via a contact electrode provided between the main body upper portion 12 and the main body lower portion 11.

As illustrated in FIG. 1, a liquid storage 17 having a semicircular or substantially semicircular planar shape is provided in a rear half region of the upper surface of the main body upper portion 12. As illustrated in FIG. 2, the liquid storage 17 includes a bottom surface 17b that gradually becomes shallower toward the side of the front surface. Further, a liquid supply path 18 to supply liquid (medical liquid) from the liquid storage 17 toward the vibration surface 43 of the vibration portion 40 is connected to a front surface of the liquid storage 17. The liquid storage 17 and the liquid supply path 18 define a liquid supply portion. In the exploded state in FIGS. 1 and 2, the liquid storage 17 is open upward. Therefore, the user may insert the medical liquid into the liquid storage 17 from above.

A cover 31 having an elliptical or substantially elliptical plate shape is connected to the rear edge of the upper surface of the main body upper portion 12 so as to be rotatable with respect to the main body upper portion 12 as indicated by an arrow B via a hinge 38. The cover 31 includes a protrusion 33 having a cylindrical or substantially cylindrical shape and a mesa portion 34 having a semicircular or substantially semicircular planar shape corresponding to the planar shape of the liquid storage 17, on the side facing the upper surface of the main body upper portion 12. As will be described later, in the state where the cover 31 closes the main body upper portion 12 and the nebulizer 1 is assembled, the protrusion 33 functions to position the exchangeable member 20. Further, the mesa portion 34 closes the upper portion of the liquid storage 17, thus preventing the medical liquid from overflowing from the liquid storage 17.

An engagement frame 32 having a letter U shape or substantially a letter U shape is attached to a tip (the end on the side opposite to the hinge 38) of the cover 31 so as to be rotatable with respect to the cover 31 via a hinge 39 as indicated by an arrow C. In the state where the cover 31 closes the main body upper portion 12, when the engagement frame 32 is rotated toward the front surface of the main body upper portion 12, the engagement frame 32 engages with an engagement protrusion 19 provided on the upper portion of the front surface of the main body upper portion 12. As a result, the cover 31 is fixed in a closed state with respect to the main body upper portion 12. The cover 31 and the engagement frame 32 define a cap 30. With this configuration, the user can easily open and close the cap 30 with respect to the main body 10 (the main body upper portion 12), and prevent the cap 30 from being lost.

FIGS. 1 and 2 illustrate the exchangeable member 20 separated from the main body 10 and the cap 30. When the nebulizer 1 is used, the exchangeable member 20 is detachably attached to the concave portion 16 of the main body upper portion 12 in advance.

Figures 8A, 8B, 8C, 8D:
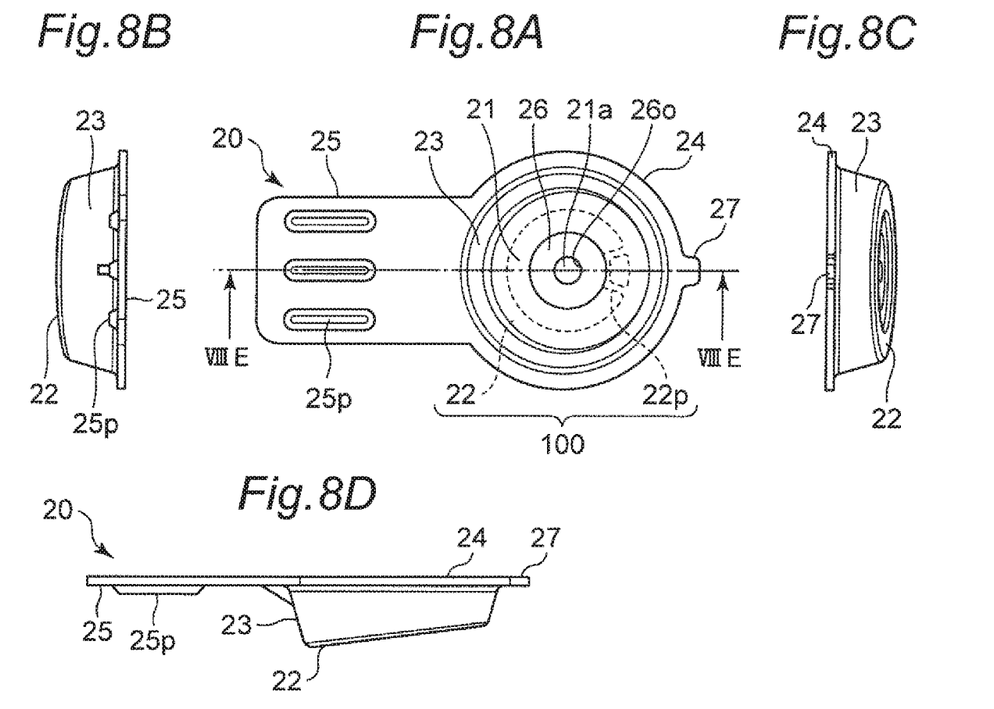
FIG. 8A is a plan view illustrating the exchangeable member.
FIGS. 8B, 8C and 8D are views illustrating the exchangeable members when viewed from left, right, and below in FIG. 8A, respectively.
Figure 8E:
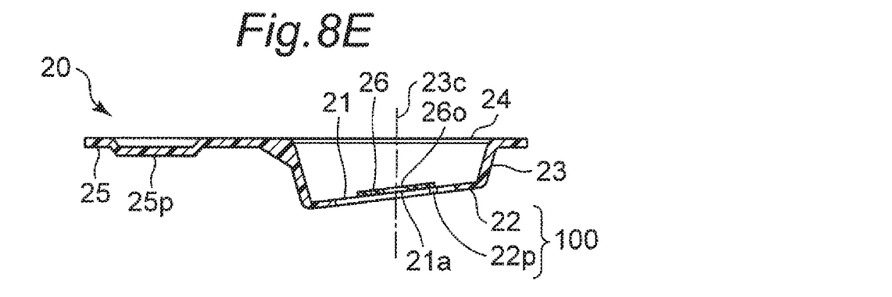
FIG. 8E is a sectional view taken along a line VIIIE-VIIIE in FIG. 8A.

FIGS. 8A to 8G illustrate the structure of the exchangeable member 20 in detail. As illustrated in FIGS. 8A and 8E, the exchangeable member 20 includes a flat sheet 21 to be faced to the vibration surface 43 (see FIGS. 1 and 2), a flat annular bottom plate 22 that supports a lower surface of a peripheral edge of the sheet 21 and has an inner diameter larger than the diameter of the vibration surface 43, a side wall portion 23 that is continuous to an outer edge of the bottom plate 22 and is to be faced to the side surface 16c of the concave portion 16 (see FIGS. 1 and 2), and a flange 24 that is continuous to an upper edge of the side wall portion 23 and radially extends outward from the upper edge. The sheet 21 is attached to an upper surface of the bottom plate 22 by adhesion or welding. That is, the bottom plate 22 is present only on a side of the lower surface of the sheet 21.

A mesh portion 21a is provided in a central region or in a substantially central region of the sheet 21.

Figures 8F, 8G:
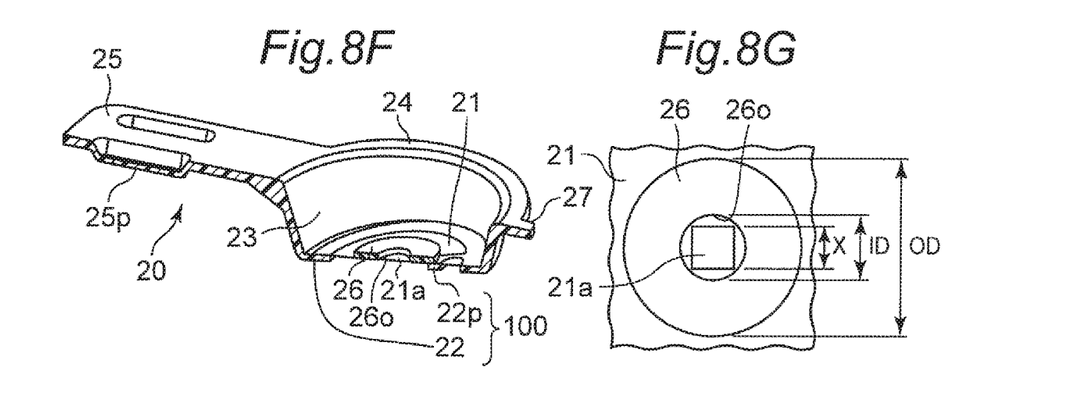
FIG. 8F is a perspective view illustrating the cut surface when the exchangeable member is cut along the line VIIIE-VIIIE in FIG. 8A.
FIG. 8G is an enlarged view illustrating the vicinity of the mesh portion in FIG. 8A.

As illustrated in FIGS. 8E and 8F, the mesh portion 21a and the bottom plate 22 of the exchangeable member 20 has a substantially flat inclined surface inclined with respect to a plane (horizontal plane) orthogonal to a center 23c of the side wall portion 23 so as to correspond to the bottom surface 16b of the concave portion 16 of the main body 10 (see FIG. 2). Further, the side wall portion 23 of the exchangeable member 20 gradually opens toward the upper side so as to correspond to the side surface 16c of the concave portion 16 of the main body 10 (see FIG. 2). Further, a protrusion 22p radially protrudes (projects) inward from the bottom plate 22 and reaches just below a ring 26 described later. The bottom plate 22 and the protrusion 22p define a support frame 100. With this configuration, the sheet 21 is able to be maintained as flat as possible. Further, as will be described later, the protrusion 22p defines and functions as a portion of the support frame 100 to maintain the sheet 21 with respect to the vibration surface 43 at an inclination angle.

Further, the protrusion 22p and the bottom plate 22 are made of the same material, continuously and uniformly integrated. Thus, the vibration surface 43 and the mesh portion 21a are able to be accurately inclined in the attached state without increasing the number of members for inclining. Therefore, the configuration becomes simpler.

FIG. 8G is an enlarged view illustrating the vicinity of the mesh portion 21a in FIG. 8A. In this example, the mesh portion 21a includes a large number of through-holes not illustrated having a diameter of about 3 μm in a square region with a side dimension X=1.5 mm in the sheet 21 having a thickness of about 30 μm. A ring 26 having a flat annular shape and a thickness of about 400 μm is attached to the sheet 21 by adhesion or welding so as to surround the mesh portion 21a. Here, the ring 26 has an outer diameter smaller than the inner diameter of the bottom plate 22. The ring 26 is attached to maintain the mesh portion 21a as flat as possible and to adjust the natural frequency of the sheet 21 including the mesh portion 21a. In this example, the ring 26 has an inner dimension ID of about 2.2 mm and an outer dimension OD of about 6.0 mm, for example. The mesh portion 21a is positioned within the opening 26o of the ring 26 so as to eject the atomized medical liquid through the above-described through holes.

As illustrated in FIGS. 8A and 8E, in the exchangeable member 20, the grip portion 25 radially extends beyond the flange 24 outward in a particular direction from the center 23c of the side wall portion 23 (in this example, leftward in FIGS. 8A and 8E). When the user holds the exchangeable member 20 by hand, the user may conveniently pick the grip portion 25, for example, with a thumb and an index finger. The grip portion 25 is provided with irregularities 25p for anti-skid. Further, in this exchangeable member 20, the tip protrusion 27 protrudes beyond the flange 24 in a direction opposite to the extending direction of the grip portion 25, in this example, rightward in FIGS. 8A and 8E. When the user attaches the exchangeable member 20 to the concave portion 16 of the main body upper portion 12, the grip portion 25 and the tip protrusion 27 enable circumferential positioning of the exchangeable member 20 with respect to the concave portion 16.

In this example, all elements defining the exchangeable member 20 are made of a synthetic resin. Therefore, the exchangeable member 20 is able to be manufactured at low cost. Examples of the synthetic resin forming the exchangeable member 20 include polyamide resin, polyester, syndio polystyrene, polysulfone, polyether sulfone, polyether ether ketone, polyether imide, polyamide imide, PPS (polyphenylene sulfide), epoxy, phenol, and polyimide.

In the state where the cap 30 is opened with respect to the main body 10 as illustrated in FIGS. 1 and 2, the user who wishes to use the mesh nebulizer 1 attaches the exchangeable member 20 having the mesh portion 21a to the concave portion 16 opened upward of the main body 10 as illustrated by an arrow D in FIG. 2.

Upon attachment of the exchangeable member 20, the user holds the grip portion 25 by hand (for example, vertically picks the grip portion 25 with the thumb and the index finger), thus easily attaching the exchangeable member 20 to the concave portion 16 of the main body 10 without touching the mesh portion 21a of the exchangeable member 20 with any finger.

Further, at attachment of the exchangeable member 20, the user adjusts the tip protrusion 27 and the grip portion 25 of the exchangeable member 20 to the groove 16f and the groove 16e around the upper edge of the concave portion 16, respectively, thus enabling circumferential positioning of the exchangeable member 20 with respect to the concave portion 16.

As described above, the side surface of the concave portion 16 of the main body 10 gradually opens as toward the upper side. Further, the side wall portion 23 of the exchangeable member 20 gradually opens toward the upper side so as to correspond to the side surface 16c of the concave portion 16 of the main body 10 (see FIG. 2). Therefore, upon attachment of the exchangeable member 20, when the user places the exchangeable member 20 near the concave portion 16, the side wall portion 23 of the exchangeable member 20 is guided downward by the side surface 16c of the concave portion 16.

Further, the bottom surface 16b of the concave portion 16 of the main body 10 is inclined with respect to the longitudinal axis direction (vertical direction) of the main body 10, and the mesh portion 21a and the bottom plate 22 of the exchangeable member 20 are inclined with respect to the center 23c of the side wall portion 23 so as to correspond to the bottom surface 16b of the concave portion 16 of the main body 10. Therefore, at attachment of the exchangeable member 20, when the user places the exchangeable member 20 near the concave portion 16, the mesh portion 21a and the bottom plate 22 of the exchangeable member 20 are guided so as to correspond to the bottom surface 16b of the concave portion 16 of the main body 10. This aids positioning of the exchangeable member 20 with respect to the concave portion 16 in the circumferential direction and the longitudinal axis direction.

Figure 3:
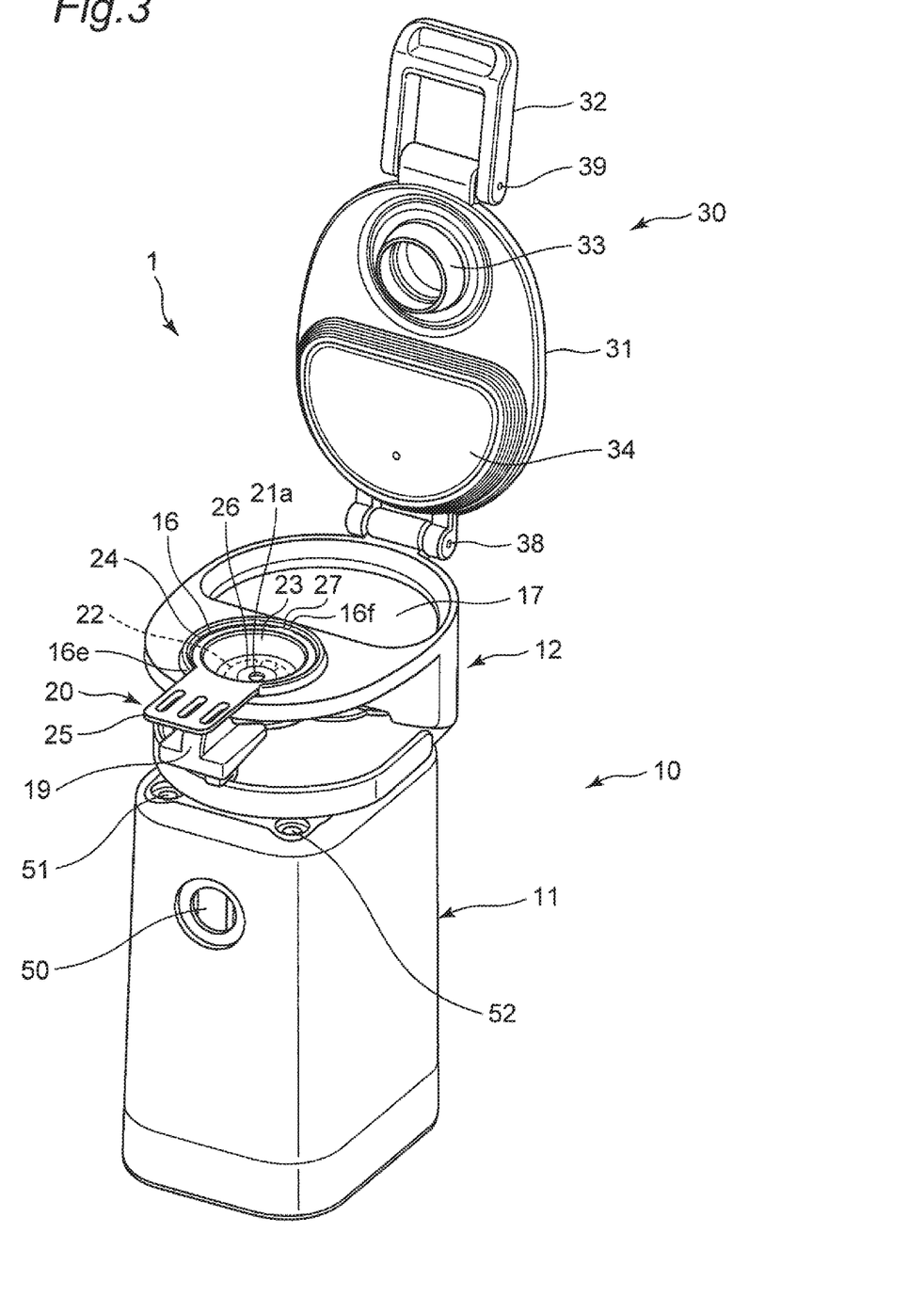
FIG. 3 is a perspective view illustrating a state where an exchangeable member including a mesh portion is attached to the mesh nebulizer (attached state).
Figure 4:
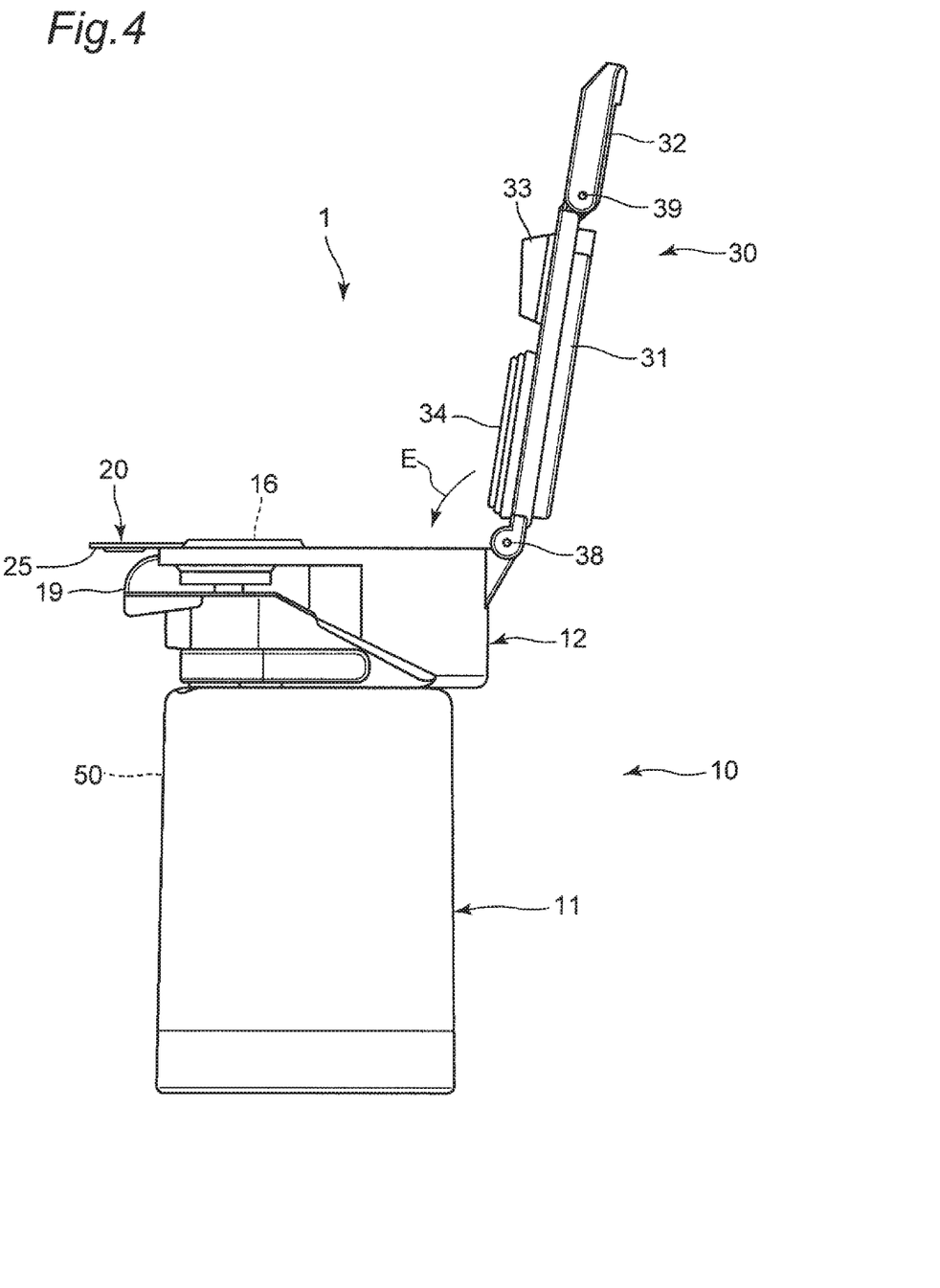
FIG. 4 is a view illustrating the mesh nebulizer in the attached state in FIG. 3 when viewed from a right side.

As a result, as illustrated in FIGS. 3 and 4, the bottom plate 22 (supporting the peripheral edge of the mesh portion 21a) of the exchangeable member 20 faces the bottom surface 16b of the concave portion 16, and the side wall portion 23 of the exchangeable member 20 faces the side surface 16c of the concave portion 16. Therefore, the user can easily attach the exchangeable member 20 to the concave portion 16 of the main body 10. This state is called an attached state.

Figures 5A, 5B:
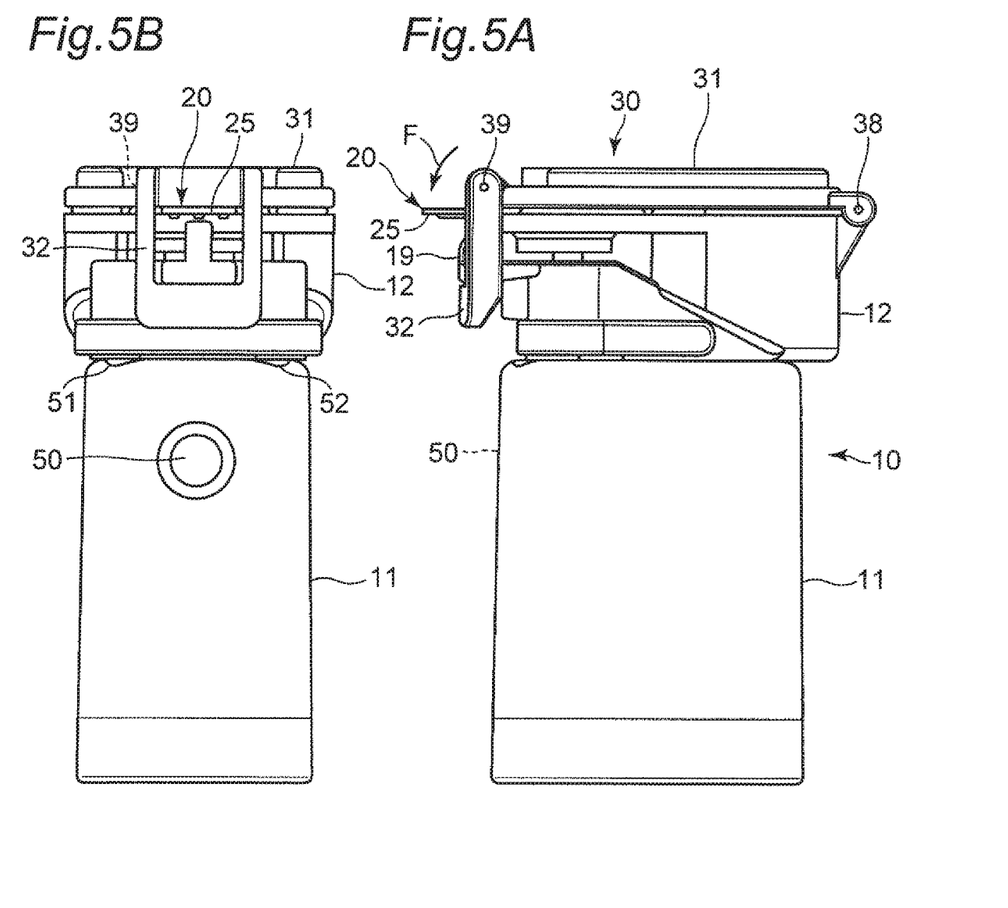
FIG. 5A is a view illustrating a state where the mesh nebulizer is assembled (assembled state) when viewed from a right side.
FIGS. 5B and 5C are views illustrating the mesh nebulizer of FIG. 5A when viewed from the front and above, respectively.
Figure 5C:
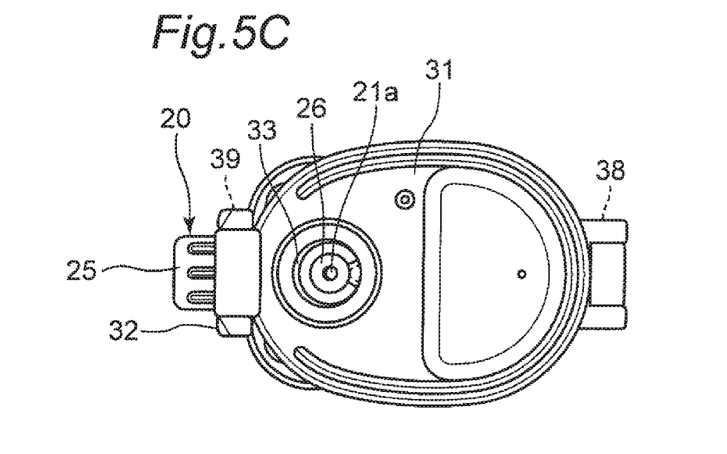

In the attached state, the user closes the cap 30 with respect to the main body 10. Specifically, the user closes the cover 31 with respect to the main body upper portion 12 as indicated by an arrow E in FIG. 4. Further, in the state where the cover 31 is closed with respect to the main body upper portion 12, the user rotates an engagement frame 32 toward the front surface of the main body upper portion 12 as indicated by an arrow F in FIG. 5A. Then, the engagement frame 32 passes over the grip portion 25 of the exchangeable member 20 and engages with an engagement protrusion 19 provided on the upper portion of the front surface of the main body upper portion 12. As a result, the cover 31 is fixed in a closed state with respect to the main body upper portion 12. In this way, the mesh nebulizer 1 is easily assembled. This state is called an assembled state. FIGS. 5B and 5C illustrate the mesh nebulizer in FIG. 5A when viewed from front and above, respectively. Further, FIG. 6 is a longitudinal sectional view illustrating the mesh nebulizer 1 in the assembled state when viewed from right.

In this assembled state, the mesa portion 34 of the cover 31 closes the upper portion of the liquid storage 17, preventing the medical liquid from overflowing from the liquid storage 17.

Figure 6:
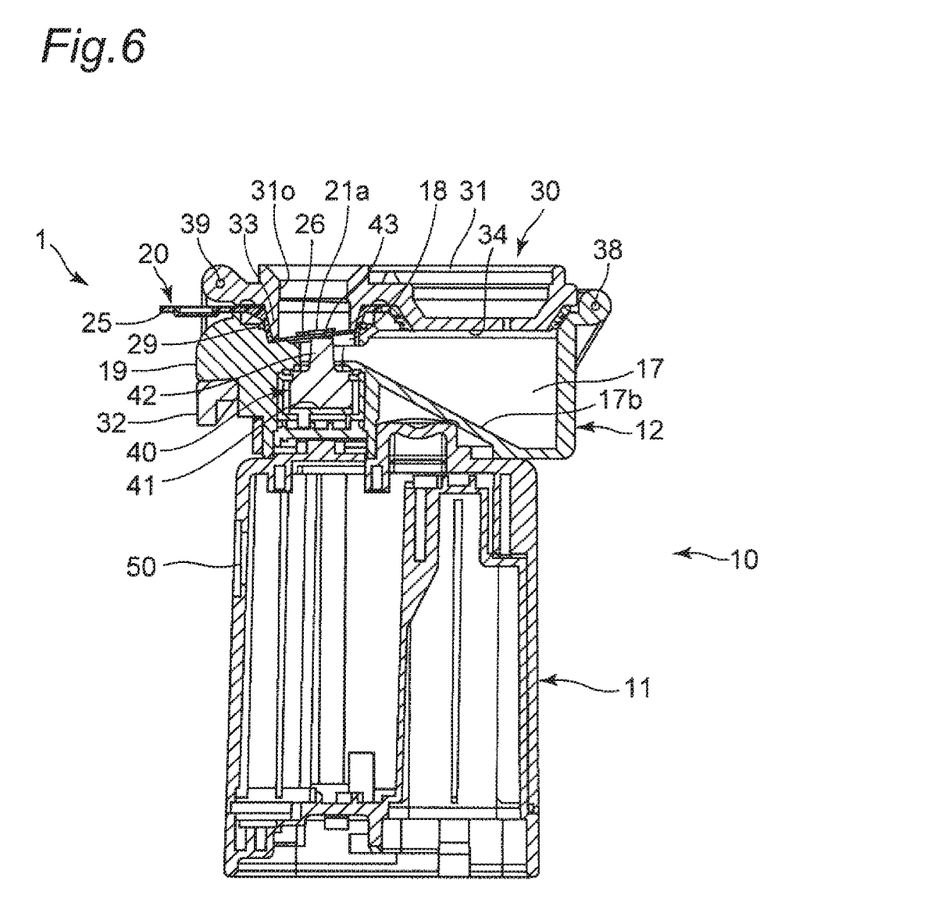
FIG. 6 is a longitudinal cross section illustrating the mesh nebulizer in the assembled state when viewed from a right side.
Figure 7A:
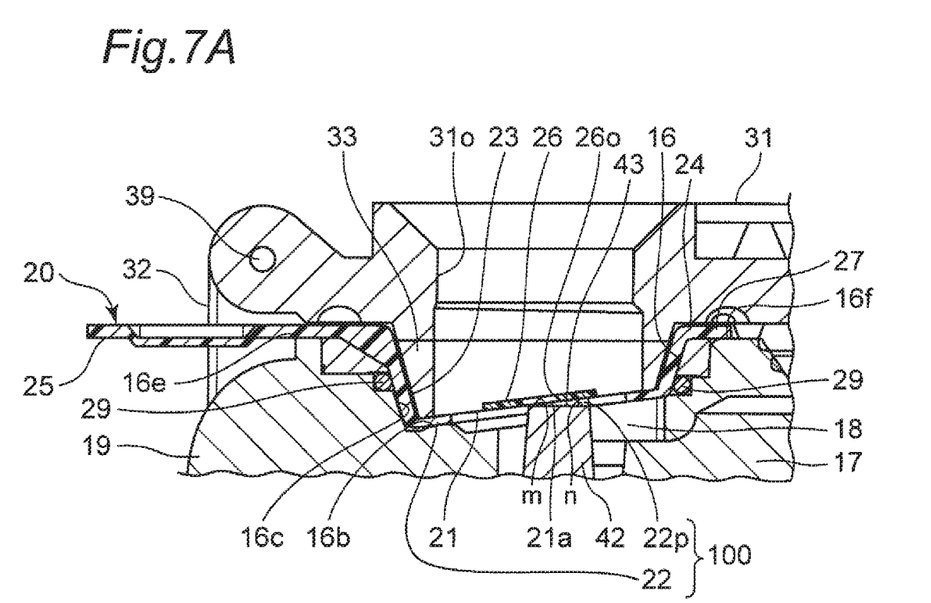
FIG. 7A is an enlarged view illustrating the vicinity of the exchangeable member in FIG. 6.
Figure 7B:
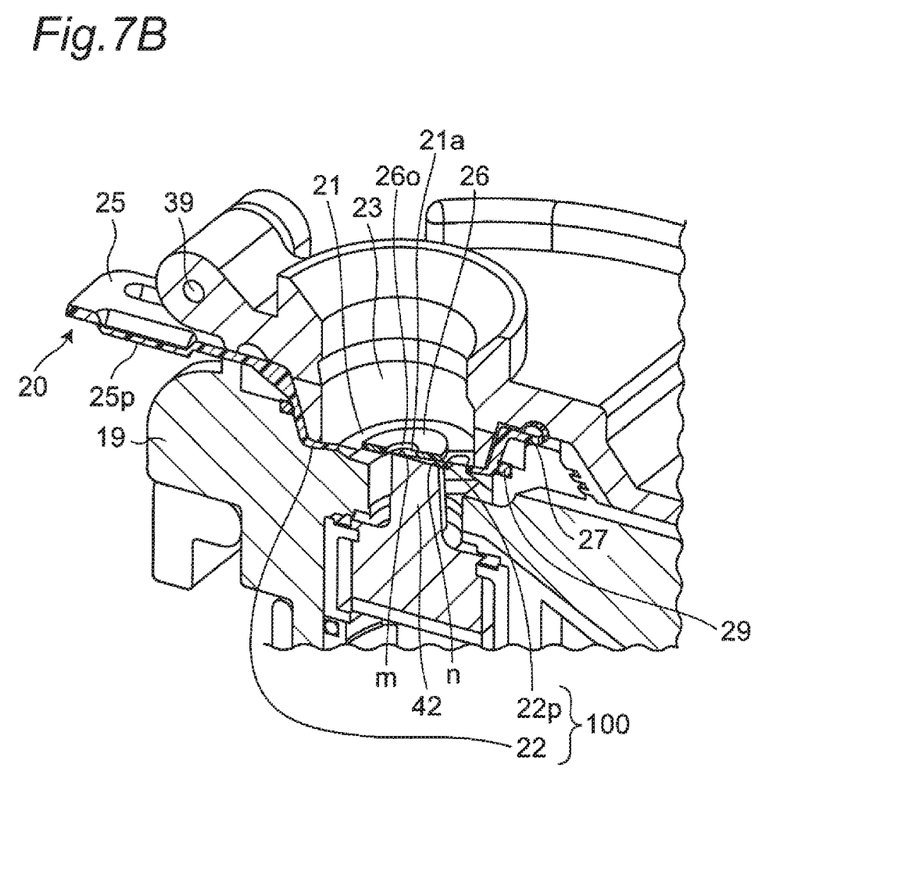
FIG. 7B is a perspective view illustrating a longitudinal sectional cut surface of the mesh nebulizer in FIG. 6.

FIG. 7A is an enlarged view illustrating the vicinity of the exchangeable member in FIG. 6. FIG. 7B is a perspective view illustrating a longitudinal sectional cut surface of the mesh nebulizer in FIG. 6. As illustrated in FIGS. 7A and 7B, a protrusion 33 of the cap 30, the protrusion 33 protruding toward the main body upper portion 12, presses the bottom plate 22 of the exchangeable member 20 onto the bottom surface 16b of the concave portion 16, to position the exchangeable member 20 in the longitudinal axis direction of the main body 10. As a result, the mesh portion 21a of the exchangeable member 20 faces the vibration surface 43 of the vibration portion 40 located at a position corresponding to the bottom surface 16b of the concave portion 16.

In this assembled state, the sheet 21 including the mesh portion 21a faces the vibration surface 43 of the main body 10 at an angle, and is in contact with a first portion m of the peripheral edge of the vibration surface 43, and the protrusion 22p of the support frame 100 is in contact with a second portion n of the peripheral edge of the vibration surface 43, the second portion n opposing the first portion m, and the protrusion 22p maintains the sheet 21 with respect to the vibration surface 43 at the angle. With this configuration, the sheet 21 including the mesh portion 21a is directly positioned with respect to the vibration surface 43 by the first portion m, and is indirectly positioned with respect to the vibration surface 43 via the protrusion 22p of the support frame 100 by the second portion n. As a result, the inclination accuracy of the sheet 21 including the mesh portion 21a with respect to the vibration surface 43 of the ultrasonic vibrator 41 is improved without increasing the number of elements or members. Therefore, at use, the mesh portion 21a is accurately inclined with respect to the vibration surface 43, so that the gap between the mesh portion 21a and the vibration surface 43 is able to be improved or optimized at some position of the mesh portion 21a. Therefore, the liquid is able to be stably atomized at all times. Since the sheet 21 including the mesh portion 21a is in direct or indirect contact with the peripheral edge of the vibration surface 43, the influence of the vibration to the vibration surface 43 is small.

Further, the protrusion 22p as a portion of the support frame 100 is in contact with the second portion n of the peripheral edge of the vibration surface 43. As a result, the protrusion 22p is reliably in contact with the second portion n of the peripheral edge of the vibration surface 43, so that the mesh portion 21a is able to be reliably inclined with respect to the vibration surface 43.

In addition, as described above, the packing 29 is provided on the side surface 16c of the concave portion 16 of the main body 10 so as to circumferentially surround the side wall portion 23 of the exchangeable member 20. In below-mentioned use, the packing 29 prevents the medical liquid supplied between the vibration surface 43 and the mesh portion 21a from overflowing to the outside through a gap between the side surface 16c of the concave portion 16 and the side wall portion 23 of the exchangeable member 20.

Figure 9:
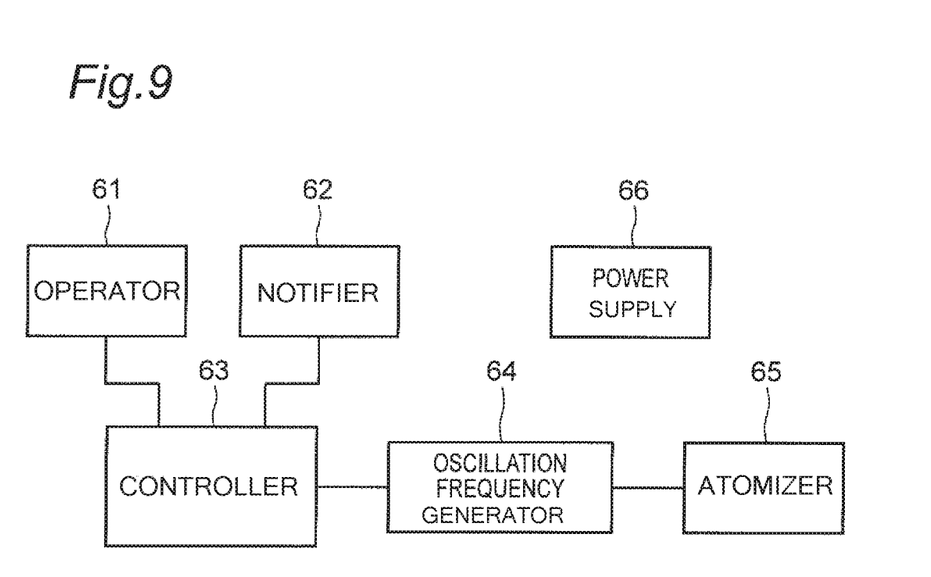
FIG. 9 is a block diagram illustrating a control system mounted on a main body of the mesh nebulizer.

FIG. 9 is a block diagram illustrating a control system mounted on the main body 10 of the mesh nebulizer 1. The mesh nebulizer 1 includes an operator 61, a notifier 62, a controller 63, an oscillation frequency generator 64, an atomizer 65, and a power supply 66. In this example, the operator 61 includes a power switch 50 illustrated in FIG. 1. In this example, the notifier 62 includes LED lamps 51 and 52 illustrated in FIG. 1, and may further include a buzzer not illustrated. The oscillation frequency generator 64 applies an AC drive voltage to the atomizer 65 based on a control signal from the controller 63. This drive voltage is output, for example, over a certain output time after the power switch 50 is pressed. The output time can be measured by a timer not illustrated. The atomizer 65 includes the vibration portion 40 and the mesh portion 21a of the exchangeable member 20 in FIG. 1. The AC drive voltage from the oscillation frequency generator 64 is applied to the ultrasonic vibrator 41 of the vibration portion 40 of the atomizer 65. The vibration of the ultrasonic vibrator 41 is amplified by the horn 42 and transmitted to the vibration surface 43. When the vibration surface 43 vibrates, the medical liquid supplied to the gap between the vibration surface 43 and the mesh portion 21a is atomized through the mesh portion 21a and is ejected. The controller 63 includes a CPU (Central Processing Unit) and sends a signal to the atomizer 65 via the oscillation frequency generator 64 to control the atomization amount, the continuous operation time, and the like. In addition, the controller 63 informs that the power is turned on by lighting of the LED lamp 51, that the capacity of the battery is insufficient by blinking of the LED lamp 52, and the like. The power supply 66 includes a battery (for example, a rechargeable battery that can charge and discharge DC 3V), and supplies power to each element or portion of the control system.

Figure 10:
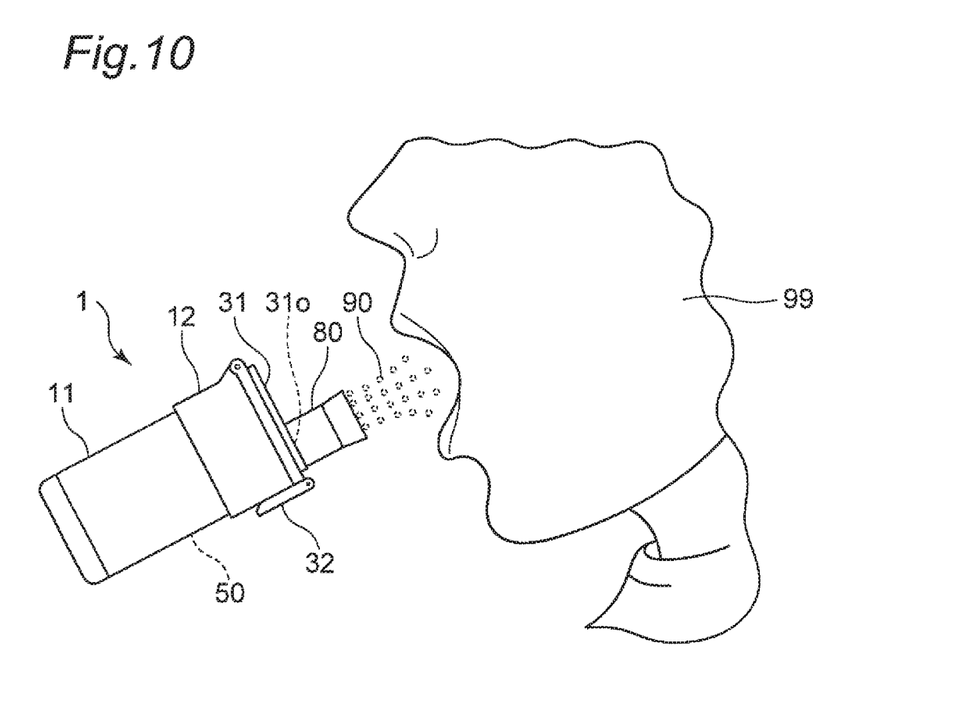
FIG. 10 is a diagram illustrating a mode in which the user uses the mesh nebulizer.

When using this mesh nebulizer 1, the user previously fills the medical liquid in the liquid storage 17 of the main body upper portion 12. Then, as illustrated in FIG. 10, the user detachably attaches, for example, a mouthpiece 80 to an opening 310 in the protrusion 33 of the cover 31 in the assembled state. As a result, the mesh portion 21a of the exchangeable member 20 faces the vibration surface 43 of the main body 10 at an inclination angle with high accuracy. This exchangeable member 20 is typically disposable after use in the mesh nebulizer 1. In this case, the user does not need to clean, disinfect, and dry the exchangeable member 20 including the mesh portion 21a. Accordingly, for the user, care is easy. Further, since the exchangeable member 20 is configured to be separated from the main body 10 and the cap 30, it can be manufactured relatively inexpensively and at a relatively small size. Therefore, for the user, costs for the exchangeable member 20 are reduced. Instead of the mouthpiece 80, an inhalation mask covering the face of a user 99 may be attached.

As illustrated in FIG. 10, when the user slightly inclines the mesh nebulizer 1 to the near side, the medical liquid is supplied from the liquid storage 17 of the liquid supply portion to the vibration surface 43 of the vibration portion 40 through the liquid supply path 18. That is, the medical liquid is supplied between the vibration surface 43 and the mesh portion 21a. Then, when the user turns on the power switch 50, a drive voltage is applied to the ultrasonic vibrator 41 of the vibration portion 40, vibrating the vibration surface 43. As a result, the medical liquid 90 is atomized and ejected through the mesh portion 21a (more precisely, a plurality of through holes penetrating the sheet 21).

In this preferred embodiment, the protrusion 22p and the bottom plate 22 preferably are made of the same material, continuously and uniformly integrated, but the present invention is not limited thereto. For example, the protrusion 22p may be a separate body from the bottom plate 22, and may be attached to the bottom plate 22 by welding or adhesion, for example. In this case, the bottom plate 22 and the protrusion 22p may be separately manufactured. Therefore, the support frame 100, in turn, the exchangeable member 20 may be easily manufactured.

As described above, a mesh nebulizer according to a preferred embodiment of the present disclosure is a mesh nebulizer that atomizes and ejects liquid through a mesh portion, the mesh nebulizer including a vibration portion including a vibration surface facing upward, a liquid supply portion that supplies liquid toward the vibration surface of the vibration portion, a sheet including the mesh portion, and a support frame that supports a peripheral edge of the sheet, wherein the support frame includes a bottom plate that supports a lower surface of the peripheral edge of the sheet, the bottom plate having a flat annular shape, and a larger inner diameter than a diameter of the vibration surface, and a protrusion radially protruding inward from the bottom plate, the sheet including the mesh portion faces the vibration surface with an inclination angle and is in contact with a first portion of a peripheral edge of the vibration surface, and the protrusion of the support frame is in contact with a second portion of the peripheral edge of the vibration surface, the second portion opposing the first portion, and maintains the sheet with respect to the vibration surface at the inclination angle.

In the present specification, the "mesh portion" means a component that includes a plurality of through-holes penetrating the sheet and allows liquid to pass through these through-holes and atomizes the liquid.

In a mesh nebulizer of a preferred embodiment of the present disclosure, the sheet including the mesh portion faces the vibration surface at the inclination angle, and is in contact with the first portion of the peripheral edge of the vibration surface. The protrusion of the support frame is in contact with the second portion of the peripheral edge of the vibration surface, the second portion opposing the first portion, and maintains the sheet with respect to the vibration surface at the inclined angle. Therefore, the sheet including the mesh portion is directly positioned with respect to the vibration surface by the first portion, and is indirectly positioned with respect to the vibration surface via the portion of the support frame. As a result, the inclination accuracy of the sheet including the mesh portion with respect to the vibration surface of the horn vibrator is improved without increasing the number of elements or members.

At use, the liquid supply portion supplies the liquid toward the vibration surface of the vibration portion. This supplies the liquid between the vibration surface and the mesh portion. Then, a drive voltage is applied to the vibration portion, vibrating the vibration surface. Thus, the liquid is atomized and ejected through the mesh portion (more precisely, a plurality of through holes penetrating the sheet). Here, since the mesh portion is accurately inclined with respect to the vibration surface, the gap between the mesh portion and the vibration surface may be improved or optimized at some position of the mesh portion. Therefore, the liquid may be stably atomized at all times. Since the sheet including the mesh portion is in direct or indirect contact with the peripheral edge of the vibration surface, the influence of the vibration of the vibration surface is small.

A mesh nebulizer according to one preferred embodiment of the present disclosure further includes a main body including a concave portion opened upward, wherein the main body includes the vibration portion including the vibration surface arranged at a position corresponding to a bottom surface of the concave portion, a cap that openably covers an upper portion of the main body, and an exchangeable member separated from the main body and the cap, the exchangeable member being detachably attached into the concave portion in advance when the nebulizer is used, and the exchangeable member includes the sheet including the mesh portion and the support frame that supports the peripheral edge of the sheet.

A user who wishes to use the mesh nebulizer of this preferred embodiment detachably attaches the exchangeable member including the mesh portion to the concave portion opened upward of the main body in the state where the cap is opened with respect to the main body. Thus, the mesh portion of the exchangeable member faces the vibration surface of the main body at the inclination angle with high accuracy. This exchangeable member is typically disposable after use in the mesh nebulizer. In this case, the user does not need to clean, disinfect, and dry the exchangeable member including the mesh portion. Accordingly, for the user, care is easy. In addition, since the exchangeable member is configured to be separated from the main body and the cap, it may be manufactured relatively inexpensively and with relatively small size. Therefore, for the user, costs for the exchangeable member are reduced.

In a mesh nebulizer according to one preferred embodiment of the present disclosure, the protrusion and the bottom plate are made of same material, continuously and uniformly integrated.

Here, "made of same material, continuously and uniformly integrated" means, for example, the case where a plurality of elements or parts are integrally molded by injection molding.

In the mesh nebulizer according to this preferred embodiment, the mesh portion is able to be accurately inclined with respect to the vibration surface without increasing the number of members for inclining. Therefore, the configuration becomes simpler.

In a mesh nebulizer according to one preferred embodiment of the present disclosure, the protrusion is configured as a separate body from the bottom plate and attached to the bottom plate.

Here, "configured as a separate body" and "attached" means, for example, the case where a plurality of elements or parts are integrated by welding or adhesion.

In the mesh nebulizer according to this preferred embodiment, the bottom plate and the protrusion may be separately manufactured. Therefore, the support frame, in turn, the exchangeable member may be easily manufactured, and manufacturing costs may be reduced.

In a mesh nebulizer according to a preferred embodiment of the present disclosure, a ring having a flat shape and a smaller outer diameter than the inner diameter of the bottom plate is attached to an upper surface of the sheet.

In the mesh nebulizer according to this preferred embodiment, the mesh portion is maintained more flatly by the ring. Therefore, the vibration surface may be inclined with respect to the mesh portion more accurately.

As is apparent from the above, a mesh nebulizer according to a preferred embodiment of the present disclosure may improve the inclination accuracy of the sheet including the mesh portion with respect to the vibration surface of the horn vibrator without increasing the number of members, thus stably atomizing liquid.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A mesh nebulizer that atomizes and ejects liquid through a mesh portion, the mesh nebulizer comprising:

a vibration portion including a vibration surface facing upward;

a liquid supply that supplies liquid toward the vibration surface of the vibration portion;

a sheet including the mesh portion; and a support frame that supports a peripheral edge of the sheet; wherein the support frame includes a bottom plate that supports a lower surface of the peripheral edge of the sheet, the bottom plate having a flat annular shape, and a larger inner diameter than a diameter of the vibration surface, and a protrusion radially protruding inward from the bottom plate;

the sheet including the mesh portion faces the vibration surface with an inclination angle and is in contact with a first portion of a peripheral edge of the vibration surface; and the protrusion of the support frame is in contact with a second portion of the peripheral edge of the vibration surface, the second portion opposing the first portion, and maintains the sheet with respect to the vibration surface at the inclination angle.

2. The mesh nebulizer according to claim 1, further comprising a main body including a concave portion opened upward, wherein the main body includes:

the vibration portion including the vibration surface at a position corresponding to a bottom surface of the concave portion;

a cap that openably covers an upper portion of the main body; and an exchangeable member separated from the main body and the cap, the exchangeable member being detachably attached into the concave portion in advance when the nebulizer is used; and the exchangeable member includes the sheet including the mesh portion and the support frame that supports the peripheral edge of the sheet.

3. The mesh nebulizer according to claim 1, wherein the protrusion and the bottom plate are made of a same material, continuously and uniformly integrated.

4. The mesh nebulizer according to claim 1, wherein the protrusion is a separate body independent from the bottom plate and attached to the bottom plate.

5. The mesh nebulizer according to claim 1, wherein a ring having a flat shape and a smaller outer diameter than the inner diameter of the bottom plate is attached to an upper surface of the sheet.

* * * * *